United States Patent [19]
Nowak et al.

[11] Patent Number: 4,876,387
[45] Date of Patent: Oct. 24, 1989

[54] PROCESS FOR PREPARING 2,4,5-TRIFLUOROBENZOIC ACID

[75] Inventors: Deanne M. Nowak, Depew; Henry C. Lin, Grand Island, both of N.Y.

[73] Assignee: Occidental Chemical Corporation, Niagara Falls, N.Y.

[21] Appl. No.: 315,763

[22] Filed: Feb. 27, 1989

[51] Int. Cl.$^4$ .............................................. C02C 63/04
[52] U.S. Cl. ...................................................... 562/493
[58] Field of Search ......................................... 562/493

[56] References Cited

U.S. PATENT DOCUMENTS 4,439,620  3/1984  Klauke et al. ........................ 562/493
4,476,320  10/1984  Diehl et al. .......................... 562/493
4,791,225  12/1988  Irikura et al. ....................... 562/493

FOREIGN PATENT DOCUMENTS 77502  4/1983  European Pat. Off. .

OTHER PUBLICATIONS

Chambers, R. D. et al, J. Chem. Soc. (C) 2394–2397, 1968.

Primary Examiner—Paul J. Killos
Attorney, Agent, or Firm—James F. Tao; Arthur S. Cookfair

[57] ABSTRACT

2,4,5-trifluorobenzoic acid is prepared by converting 4,5-di-fluoroanthranilic acid to the corresponding amine salt, converting the amine salt to the corresponding diazonium tetrafluoroborate and decomposing the tetrafluoroborate in a Schiemann reaction. In a preferred preparation, the 10 percent HCl is added to solid 4,5-difluoroanthranilic acid in sufficient amount to dissolve the solid at 70° C., the amine salt is isolated, aqueous NaNO$_2$ is added to the isolated amine salt at 0° C., followed by addition of 40 to 50 percent aqueous HBF$_4$ at 0° C., followed by separation of the tetrafluoroborate by cooling and filtering and then drying, and the dried separated tetrafluoroborate is thermally degraded to 2,4,5-trifluorobenzoic acid by heating at 125° to 140° C.

5 Claims, No Drawings

PROCESS FOR PREPARING 2,4,5-TRIFLUOROBENZOIC ACID

TECHNICAL FIELD

This invention is directed to the production of 2,4,5-trifluorobenzoic acid which is useful, for example, as an intermediate in the production of antibacterial compounds and liquid crystal components.

BACKGROUND OF THE INVENTION

Prior art discloses forming Grignard reagent in the synthesis of 2,4,5-trifluorobenzoic acid. It is not practical to scale up this reaction to industrial scale.

DeGraw, J. I. et al, Journal of Chemical and Engineering Data, Vol. 13, No. 4, pages 587–588, discloses preparing 2,4,5-trifluorobenzoic acid by hydrogenating nitro-4,5-difluorobenzoic acid (V) in the presence o concentrated hydrochloric acid to form 2-amino-4,5-difluorobenzoic acid hydrochloride (VI), esterifying the carboxyl group by reacting (VI) with methanolic hydrogen chloride, thereby to form methyl 2-amino-4,5-difluorobenzoate hydrochloride (VII), converting VII to methyl 2,4,5-trifluorobenzoate (IX) by forming the diazonium fluoroborate and decomposing in a Schiemann reaction, the hydrolyzing (IX) to form 2,4,5-trifluorobenzoic acid. It has been discovered herein that the route of DeGraw et al can be substantially simplified by starting out with 4,5-difluoroanthranilic acid and converting to the diazonium fluoroborate without an intermediate step of esterifying the carboxyl group. The starting material 4,5-difluoroanthranilic acid is readily prepared, for example, as taught in Fifolt U.S. Pat. No. 4,521,616.

SUMMARY OF THE INVENTION

The process herein comprises the steps of:
(a) reacting 4,5-difluoroanthranilic acid with a mineral acid to form the corresponding amine salt;
(b) converting said amine salt to the corresponding diazonium tetrafluoroborate (i.e., without the intermediate step of esterifying the carboxyl group of said amine salt); and
(c) thermally degrading said tetrafluoroborate, i.e., heating it to cause decomposition, to form 2,4,5-trifluorobenzoic acid.

DETAILED DESCRIPTION

Step (a) is preferably carried out by admixing aqueous mineral acid with 4,5-difluoroanthranilic acid, very preferably by introducing the aqueous mineral acid into a body or stream of the 4,5-difluoroanthranilic acid. Suitable mineral acids include, for example, HCl, $H_2SO_4$, $HBF_4$ and HF, and the mineral acid which is used determines the anionic counterion of the amine salt formed. Ten percent HCl is a preferred mineral acid reagent. Stoichiometric amounts of mineral acid reagent are preferably used but if desired up to twice stoichiometric amounts or greater can be used. The reaction of step (a) is normally carried out at a temperature ranging from 0° C. to about 100° C. and preferably from 60° C. to 80° C. Since the reaction is exothermic, the temperature is readily controlled by heating to a predetermined temperature and then cooling during reaction to maintain a suitable temperature. The time of reaction is normally about 5 minutes to about 1 hour depending on the scale and the extent of stirring. The amine salt product is formed in solution but is readily recovered in solid form by cooling, e.g., in a dry ice/methylene chloride bath and filtering and/or by stripping. Isolation of said product is preferred at this point to reduce carryover of impurities into succeeding reaction steps.

Step (b) preferably comprises reacting an aqueous diazotization agent with the amine salt product of step (a), e.g., by adding the aqueous diazotization agent to a receptacle containing the amine salt to form a reaction mixture and then reacting with aqueous hydrofluoroboric acid ($HBF_4$), e.g., by introducing the aqueous $HBF_4$ into reaction mixture in said receptacle. Stoichiometric amounts of diazotization and $HBF_4$ reactants are preferably used but if desired up to twice stoichiometric or higher amounts can be used. The reactions of step (b) preferably are carried out at temperatures ranging from 0° C. to 5° C. Since the reaction is exothermic, cooling is necessary to maintain the desired temperature range. The diazotization agent can be, for example, sodium nitrite, potassium nitrite or nitrous acid or other precursor of nitrite ion. The aqueous hydrofluoroboric acid is preferably 40 to 50 percent $HBF_4$. Step (b) is readily carried out over a time period, for example, of 10 minutes to 1 hour. The fluoroborate product of step (b) is readily isolated, e.g., by cooling and filtering, and preferably is dried prior to effecting step (c).

In step (c), the diazonium tetrafluoroborate product of step (b), namely

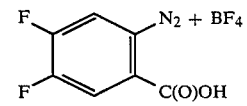

is thermally degraded to the desired product, namely 2,4,5-trifluorobenzoic acid with the concurrent production of gaseous byproducts $N_2$ and $BF_3$. This step can be carried out, for example, by heating at 100° C. to 200° C. and preferably at 125° C. to 140° C. Gas release, e.g., nitrogen release, signals occurrence of the decomposition.

The process herein is illustrated in the following working example. The reactions of the example can be summarized as follows:

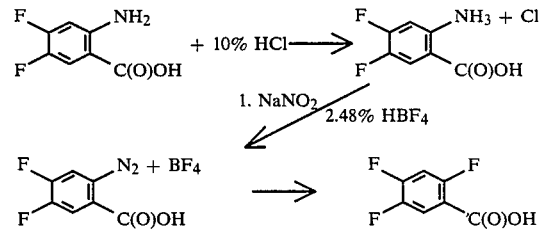

EXAMPLE

A 3-necked, 5 ml round bottomed flask equipped with a thermometer, cold-water condenser and magnetic stirrer is charged with 0.25 g 4,5-difluoroanthranilic acid. The contents are heated to 70° C. utilizing a water bath. Then 1.5 ml of 10 percent HCl is slowly added (the minimum amount necessary to dissolve, the solid) over a period of approximately 10 minutes. The reaction mixture is cooled in a dry ice/methylene chloride bath to obtain a tan solid precipitate which is recovered as product by filtering. Other product is recovered by stripping the filtrate. The products are combined for treatment in the next step.

Combined product (0.29 g tan solid) was cooled to 0° C. in a 3-necked 5 ml flask equipped with a thermometer, condenser and magnetic stirrer. 0.08 g $NaNO_2$ in 0.23 g distilled water was cooled to 0° C. and added to the reaction flask with external cooling. The mixture was stirred for 5 minutes. Then 0.22 g aqueous 48 percent $HBF_4$ was added dropwise. After addition, the mixture was stirred at 0° C. for 15 minutes. The mixture was then cooled to −10° C. and the solid isolated by filtration.

The isolated solid was dried at approximately 25° C./0.15 mm resulting in isolation of 0.19 g of gold-colored solids which were then heated to 140° C. in a 5 ml round-bottomed flask fitted with a dry-ice trap until $N_2$ release was no longer noted. GC/MS and $^{19}F$ NMR analyses of product confirmed the presence of 2,4,5-trifluorobenzoic acid. Essentially pure product is recovered by physical separation means, such as, crystallization.

Variations will be evident to those skilled in the art. Therefore, the scope of the invention is intended to be defined by the claims.

What is claimed is:

1. A process for preparing 2,4,5-trifluorobenzoic acid, said process comprising the steps of:

(a) reacting 4,5-difluoroanthranilic acid with a mineral acid to form the corresponding amine salt;
   (b) converting said amine salt to the corresponding diazonium tetrafluoroborate; and
   (c) heating said tetrafluoroborate to cause decomposition of it to 2,4,5-trifluorobenzoic acid.

2. A process as recited in claim 1 wherein step (a) is carried out by introducing aqueous mineral acid into a body of 4,5-difluoroanthranilic acid at a temperature ranging from about 0° C. to about 100° C., step (b) comprises forming a reaction mixture of aqueous diazotization agent and said amine salt and then introducing aqueous $HBF_4$ into said reaction mixture and is carried out at 0° to 5° C. and step (c) comprises heating at 100° to 200° C.

3. A process as recited in claim 2 wherein said tetrafluoroborate is obtained in isolated dry condition before being treated in step (c).

4. A process as recited in claim 3 wherein said mineral acid is selected from the group consisting of HCl, $H_2SO_4$, $HBF_4$ and HF and said diazotization agent is selected from the group consisting of sodium nitrite, potassium nitrite or nitrous acid.

5. A process as recited in claim 4 wherein said mineral acid is HCl, said diazotization agent is sodium nitrite and step (c) is carried out at about 125° C. to 140° C.

* * * * *